United States Patent
Born, van den et al.

(10) Patent No.: US 10,143,738 B2
(45) Date of Patent: *Dec. 4, 2018

(54) VACCINE FOR USE IN PROTECTING A PIG AGAINST PORCINE EPIDEMIC DIARRHEA VIRUS

(71) Applicants: Intervet Inc., Madison, NJ (US); Universiteit Utrecht Holding B.V., Utrecht (NL)

(72) Inventors: Erwin Born, van den, Wageningen (NL); Berend Jan Bosch, Houten (NL); Peter Rottier, Groenekan (NL)

(73) Assignees: Intervet Inc., Madison, NJ (US); Universiteit Utrecht Holding B.V., Utrecht (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/509,999

(22) PCT Filed: Sep. 11, 2015

(86) PCT No.: PCT/EP2015/070849
§ 371 (c)(1),
(2) Date: Mar. 9, 2017

(87) PCT Pub. No.: WO2016/038194
PCT Pub. Date: Mar. 17, 2016

(65) Prior Publication Data
US 2017/0304431 A1    Oct. 26, 2017

(30) Foreign Application Priority Data
Sep. 12, 2014 (EP) .................... 14184615

(51) Int. Cl.
*A61K 39/225* (2006.01)
*A61K 39/39* (2006.01)
(Continued)

(52) U.S. Cl.
CPC .......... *A61K 39/225* (2013.01); *A61K 39/215* (2013.01); *A61K 39/39* (2013.01);
(Continued)

(58) Field of Classification Search
None
See application file for complete search history.

(56) References Cited

U.S. PATENT DOCUMENTS

2004/0258701 A1* 12/2004 Dominowski ....... A61K 9/1075
424/184.1
2015/0283229 A1* 10/2015 Hernandez ............. C07K 16/10
424/186.1
2017/0304431 A1* 10/2017 Born, van den ..... A61K 39/225

FOREIGN PATENT DOCUMENTS

WO    2013152086 A1    10/2013

OTHER PUBLICATIONS

Li et al. (Emerging Infectious Diseases. Aug. 2012; 18 (8): 1350-1353).*

(Continued)

*Primary Examiner* — Shanon A. Foley

(57) ABSTRACT

The invention pertains to a vaccine for use in protecting a pig against an infection with porcine epidemic diarrhea virus (PEDV), the vaccine comprising non-live PEDV antigen and a non-metabolizable oil containing adjuvant, wherein the total amount of oil in the vaccine is less than 50% v/v, by administration of a dose of the antigen corresponding to at least 3.0E6 $TCID_{50}$ killed whole PEDV. The invention also pertains to a method of protecting a pig against an infection with porcine epidemic diarrhea virus.

10 Claims, 2 Drawing Sheets

Mean PEDV virus neutralization titres per group.

(51) Int. Cl.
  *C07K 16/10* (2006.01)
  *C07K 14/165* (2006.01)
  *A61K 39/00* (2006.01)
  *C07K 14/08* (2006.01)
  *C12N 7/00* (2006.01)
  *A61K 39/215* (2006.01)
(52) U.S. Cl.
  CPC ............ *C07K 14/165* (2013.01); *C07K 16/10* (2013.01); *A61K 2039/5252* (2013.01); *A61K 2039/545* (2013.01); *A61K 2039/552* (2013.01); *A61K 2039/55505* (2013.01); *A61K 2039/55516* (2013.01); *A61K 2039/55544* (2013.01); *A61K 2039/55566* (2013.01); *A61K 2039/575* (2013.01); *C07K 14/08* (2013.01); *C12N 7/00* (2013.01); *C12N 2770/20034* (2013.01)

(56) References Cited

OTHER PUBLICATIONS

Wang et al. (Archives of Virology. 2013; 158: 2487-2494).*
Subramaniam et al. (Journal of General Virology. 2018; 99: 230-239).*
Extended European Search report for 14184615.4 dated Feb. 6, 2015.
International Search Report for PCTEP2015070849 dated Nov. 6, 2015, 4 pages.
Jongsuk Oh et al, Immunogenicity and protective efficacy of recombinant S1 domain of the porcine epidemic diarrhea virus spike protein, Arch Virol, Jul. 10, 2014, pp. 2977-2987, vol. 159, No. 11, EP.
Lindblad, Erik B, Freund's Adjuvants, Vaccine Adjuvants, Jan. 1, 2000, pp. 49-63, XP55165850, Humana Press, EP.
Murtaugh; Dvorak; Stone. National Hog Farmer. "PEDV Immunity: Past and Present: How long does immunity last?" Sep. 2, 2014. Department of Veterinary and Biomedical Sciences, University of Minnesota, St. Paul. www.nationalhogfarmer.com.
Song et al, Porcine epidemic diarrhoea virus: a comprehensive review of molecular epidemiology, diagnosis, and vaccines, Virus genes, Jan. 22, 2012, pp. 167-175, vol. 44, No. 2, Kluwer, EP.
Sun D B et al, Spike protein region (aa 636-789) of Porcine epidemic diarrhea virus is essential for induction of neutralizing antibodie"s, Acta Virologica, Academia Prague, Jan. 1, 2007, pp. 149-156, vol. 52, No. 3, EP.
XP55165780, Die Einmal-Impfung mit der ausserordentlich langen Wirkungsdauer, -, Jan. 6, 2010, Retrieved from the Internet: URL:http://www.msd-tiergesundheit.de/binaries/2010-06_PorcilisPCV_One-Shot_Folder_P_tcm82-58526.pdf.

* cited by examiner

Mean PEDV virus neutralization titres per group.

FIGURE 1

VACCINE FOR USE IN PROTECTING A PIG AGAINST PORCINE EPIDEMIC DIARRHEA VIRUS

CROSS-REFERENCE TO RELATED APPLICATIONS

This application is a national stage entry under 35 U.S.C. § 371 of PCT/EP2015/070849 filed on Sep. 11, 2015, which claims priority to EP Application No. EP14184615.4 filed on Sep. 12, 2014. The content of PCT/EP2015/070849 is hereby incorporated by reference in its entirety.

FIELD OF THE INVENTION

The present invention pertains to a vaccine for use in protecting a pig against an infection with porcine epidemic diarrhea virus (PEDV) and to a method to protect a pig against an infection with PEDV.

BACKGROUND ART

Porcine epidemic diarrhea virus is a member of the family Coronaviridae, genus alphacoronavirus. It is a positive-sense, enveloped, single-stranded RNA virus. Porcine epidemic diarrhea (PED) was first observed among English feeder and fattening pigs in 1971. During the 1980s and 1990s, PED was prevalent throughout Europe, in countries such as Belgium, England, Germany, France, the Netherlands, and Switzerland. These outbreaks were relatively mild and could be controlled. Currently, there are no indications that PEDV is present in Europa. Severe PEDV outbreaks with high mortality are common in Asia, where it has probably become epidemic in some areas. China has seen a large increase in outbreaks since 2010 which has been attributed to the emerging of new strains, and currently PEDV is one of the main pathogens giving large economic losses in the swine industry in Asia. An Asian-like PEDV strain was for the first time introduced in the United States in April 2013 and has spread to Canada and Latin America. PEDV is most commonly transmitted via fecal-oral contact with infected swine, and may also be introduced by contaminated equipment, fomites, or personnel. Infected pigs, dirty boots, clothing, hands, equipment, or trucks can spread the disease. But there are also indications that PEDV can be transmitted through air. Sanitation and biosecurity are the best means of prevention.

In pigs, severity of disease is variable and dependent on the epidemiologic status of the herd. The primary, and often only, clinical signs are acute watery diarrhea and vomiting. In naïve animals, vomiting, acute watery diarrhea, and loss of appetite in pigs of all ages can be observed; morbidity approaches 100 percent. Particularly suckling pigs are very susceptible, and they typically display watery diarrhea, dehydration, and metabolic acidosis with mortality typically between 50 and 80 percent. On the other hand, feeder and grower pigs display diarrhea, anorexia, and depression with high morbidity, but low mortality (1-3 percent). When PEDV-infected swine are introduced to a naïve premises, clinical signs typically appear within 4-5 days. PEDV cannot spread to humans.

OBJECT OF THE INVENTION

Vaccines intended to protect a pig against an infection with PEDV are described in the art. However, actual protection is in many cases not reported, or not unambiguous reported. There is a need for a vaccine that is capable of inducing in a naive pig, virus neutralizing antibodies ("VN") to a level comparable to an antibody level that a pig obtains after wild-type infection, which vaccine at the same time is safe for the pig.

SUMMARY OF THE INVENTION

In order to meet the object of the invention, a vaccine for use as described here above in the FIELD OF THE INVENTION section has been devised, which vaccine comprises non-live PEDV antigen and a non-metabolizable oil containing adjuvant, wherein the total amount of oil in the vaccine is less than 50% v/v, by administration of a dose of the antigen corresponding to at least 3.0E6 (i.e. $3.0 \times 10^6$) $TCID_{50}$ killed whole PEDV.

It has been shown that with this vaccine the pig is safely immunized and is able to reach a VN titre which is at least comparable to a typical titre obtained in an animal surviving wild type infection with PEDV. A non-metabolizable oil, although in many cases not safe for pigs, appears to be superior over other adjuvants such as widely used metabolizable oils and aluminium hydroxide gel, and for this particular vaccine is safe when administered in a restricted amount. The typical minimum amount of the oil is 1%, but may be 2, 3, 4, 5, 6, 7, 8, 9, 10% or even higher. The minimum dose of the antigen, i.e. a dose of the antigen corresponding to at least 3.0E6 $TCID_{50}$ killed whole PEDV, has proven to be needed to obtain the required titre and is possibly even further improved by repeated vaccination as is commonly known in the art.

The invention also pertains to a method to protect a pig against an infection with porcine epidemic diarrhea virus (PEDV) comprising administering to the pig a vaccine comprising non-live PEDV antigen and a non-metabolizable oil containing adjuvant, wherein the total amount of oil in the vaccine is less than 50% v/v, and the antigen is administered at a dose corresponding to at least 3.0E6 TCID50 killed whole PEDV and to a vaccine to protect a pig against an infection with porcine epidemic diarrhea virus (PEDV) comprising non-live PEDV antigen and a non-metabolizable oil containing adjuvant, wherein the total amount of oil in the vaccine is less than 50% v/v, and the antigen is present in a dose corresponding to at least 1.5E6 TCID50 killed whole PEDV per ml.

BRIEF DESCRIPTION OF THE FIGURES

FIG. 1 shows the mean PEDV virus neutralization titers per group.

DEFINITIONS

Figures 2A, 2B:
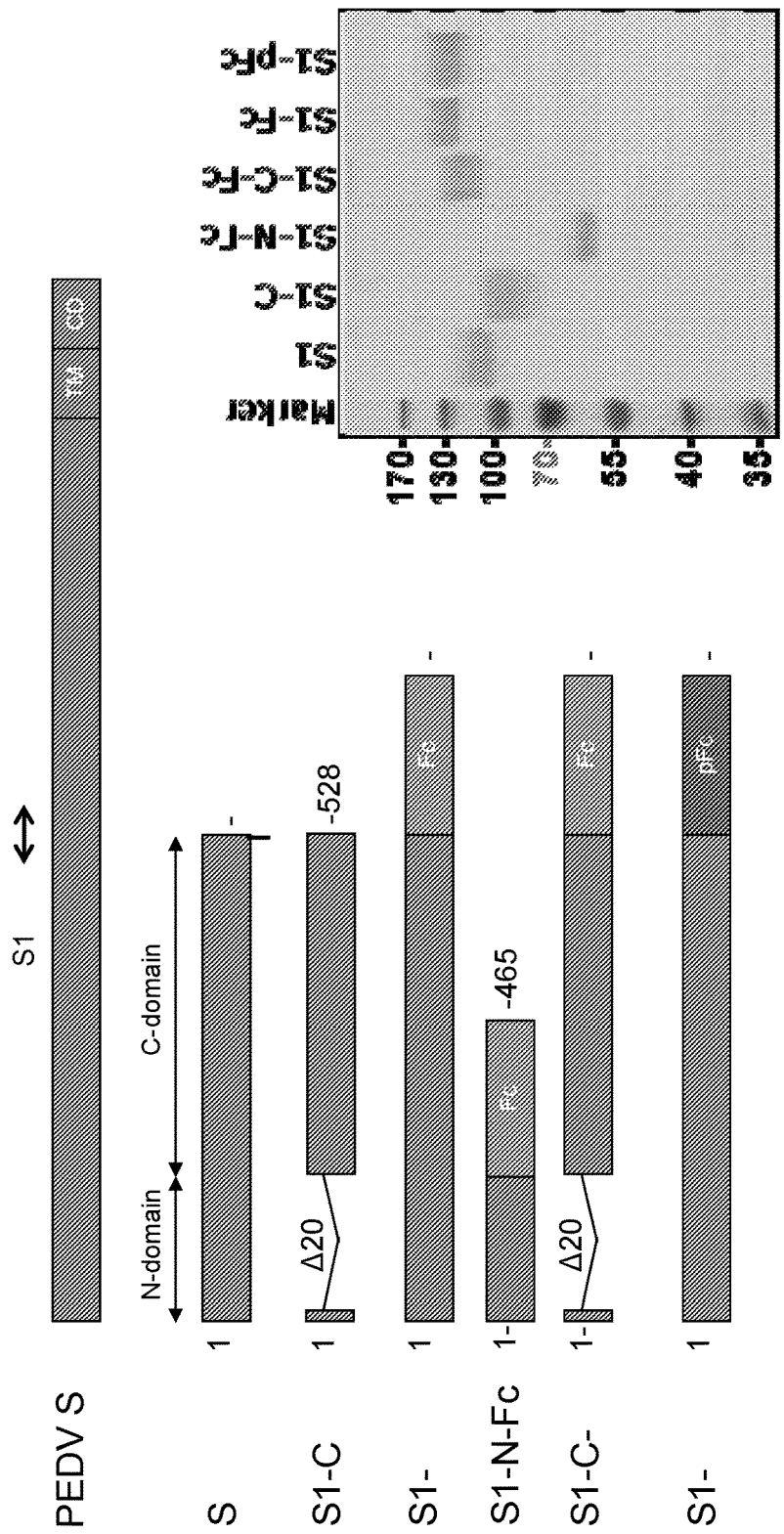
FIG. 2A displays a gel of the S1 proteins displayed in FIG. 2B below.
FIG. 2B is a schematic representation of the PEDV S1 proteins.

A vaccine is a constitution that protects against a post vaccination infection with a pathogenic micro-organism, i.e. a constitution that prevents or reduces the infection by the micro-organism, or against a clinical disease that results from the infection, typically by interfering with the micro-organism itself, for example via antibodies, in the vaccinated host. Vaccination thus prevents, or at least diminishes, the level of infection and/or prevents, or at least diminishes, the level of clinical disease resulting from that infection.

A safe vaccine is a vaccine that evokes a typical rectal temperature rise during the first 24 hours after administration of the vaccine below 2.0° C., preferably below 1.5° C., preferably below 1.0° C. and at the same time, if it gives rise to local reactions, the reactions must be mild (swellings below 10 $cm^2$, preferably below 5 $cm^2$, more preferably below 3 $cm^2$, even more preferably below 2 $cm^2$, and most preferably below 1 $cm^2$) and transient (disappear within 2 weeks, preferably within 1 week, more preferably within 3 days and most preferably within a day).

Non-live porcine epidemic diarrhea virus antigen means PEDV antigen that differs from the live (replication capable) whole virus. In particular it encompasses killed virus and subunit(s) of the virus, the latter optionally being recombinantly expressed.

A non-metabolizable oil is an oil (a liquid substance of mineral, natural or synthetic origin that cannot be freely mixed with water) that is not metabolised by a subject animal after administration, during the lifespan of the animal (for pigs this is until the pigs is 26-30 weeks of age). The oil may be distributed in the animal's body, but is not degraded by a metabolic process of the animal. Examples are mineral oils such as liquid paraffin oil or heavy mineral oil, natural oils such as squalane (hydrogenated shark liver oil) and synthetic oils such as synthetic C15-C17 hydrocarbons.

A dose of a non-live antigen corresponding to at least "X" $TCID_{50}$ killed whole PEDV means that the dose of the non-live antigen (i.e. antigen other than replication capable whole micro organism) is such that at least a VN titre is obtained with the non-live antigen that is the same as the VN titre that can be obtained with a vaccine comprising per dose "X" $TCID_{50}$ killed whole PED virus.

Killed whole virus means an antigenic constitution that results from the killing (inactivation) of live, whole virus. This does not exclude that the viral particles are, at least partly, ruptured during the inactivation or any further downstream processing.

A polypeptide that corresponds to (a part of) a protein means that the polypeptide contains at least that (part of the) protein, having a sequence homology over the length of (that part of) the protein of at least 80% with the natural occurring protein, preferably at least 81, 82, 83, 84, 85, 86, 87, 88, 89, 90, 91, 92, 93, 94, 95, 96, 97, 98, 99 up to 100% sequence homology.

The spike protein of PEDV is a large type I transmembrane protein of about 1400 amino acids long. Like other spike proteins of corona viruses, the protein is highly glycosylated. The spike protein is organized in two domains: a N-terminal domain named S1 that is responsible for receptor binding and a C-terminal S2 domain responsible for fusion.

EMBODIMENTS

In an embodiment of the vaccine for use according to the invention, the dose of the antigen corresponds to at least 1.5E7 $TCID_{50}$ killed whole PEDV. At this dose it appears to be possible to obtain titre levels that correspond to peak levels induced following wild type infection with PEDV.

In another embodiment the total amount of the oil is less than 40% v/v. Lowering the amount of oil expectedly even further increases safety. Preferably the amount of oil is between 10 and 40%, more preferably between 15 and 30%.

In still another embodiment the oil is emulsified in a hydrophilic solvent. Emulsifying the oil in a hydrophilic solvent such as for example water, expectedly further increases the safety of the vaccine.

In yet another embodiment the vaccine in addition to the non-metabolizable oil comprises vitamin E acetate. This oily, biodegradable substance may further improve vaccine efficacy and stability.

In an embodiment the antigen contains a polypeptide that corresponds to the C terminal two-third of the S1 domain of the spike protein of PEDV. This part of the PED virus has proven to be able and provide the required VN titres. Preferably the polypeptide corresponds to the S1 domain of the spike protein of PEDV or even the complete spike protein of PEDV. An easy way to present the spike protein to the immune system is to provide the antigen as killed whole PEDV.

In another embodiment the vaccine is for administration to a sow (the term "sow" does not exclude that the animal is in fact a gilt) to protect the off-spring of this sow against an infection with porcine epidemic diarrhea virus. It has appeared that the current vaccine is able to induce very high titres of antibodies. A sow is able to even further concentrate these antibodies in her colostrum and thus it is believed that the current vaccine is perfectly suitable to protect off spring of this sow against an infection with PEDV through lactation (often referred to as lactogenic immunity). Preferably the sow is vaccinated when she is pregnant, but it is also possible to vaccinate the sow right before becoming pregnant. Indeed, natural level titres can protect a pig during at least four months (see: National Hog Farmer, "*PEDV Immunity: Past and Present: How long does immunity last?*" Sep. 2, 2014 Michael Murtaugh, Cheryl Dvorak, Suzanne Stone Department of Veterinary and Biomedical Sciences, University of Minnesota, St. Paul; www.nationalhogfarmer.com) and thus, given the fact that pregnancy lasts less than 4 months, inducing high titres before becoming pregnant should be able to provide protection to the off spring via lactation.

The invention will now be further explained using the following examples.

EXAMPLES

Example 1 Virus Neutralization Assay

Sera were tested for the presence of neutralizing antibodies against PEDV using a virus neutralization (VN) assay on Vero cells. Briefly, serial two-fold dilutions of the test samples or reference sera were prepared in aMEM-TPB cell culture medium containing the antibiotics penicillin and streptomycin. Each dilution was mixed with an equal volume of 100 $TCID_{50}$ of an infectious PEDV strain that expresses green fluorescent protein (GFP) upon infection of susceptible Vero cells. After a pre-incubation period of 1 hour at 37° C., virus/serum dilution mixtures were transferred to 96-well microtitre plates containing Vero-CCL81 cells. After incubation for 48 hours at 37° C., the extent of GFP fluorescence indicative for virus replication was determined by microscopy. The antibody titre was calculated as log 2 of the reciprocal of the highest serum dilution where no virus replication could be demonstrated. Obtained VN titres are presented as averages calculated from duplicate measurements.

This way, it was established that VN titres in wild-type PEDV infected pigs that survived the infection are at a level of 5.0 log 2 per ml or higher, with peak levels at 8.0 to 9.0 log 2.

Example 2 the Influence of the Type of Adjuvant

Study Design

Twenty piglets seronegative for PEDV were available for this trial. When the piglets were approximately five weeks old they were vaccinated via the intramuscular (IM) route, and boosted two weeks thereafter. All applications were given into the neck. The vaccines contained $1.5 \cdot 10^7$ TCID$_{50}$ of 1 mM binary ethyleneimine (BEI) inactivated killed whole PEDV (cell culture adapted DR13) in 2 ml. Blood samples were collected right before the first vaccination, and one, two, three, four, and five weeks thereafter. Serum was collected from the blood samples and the virus neutralizing antibody titre was determined. Rectal temperatures were measured on the day of and one day after each vaccination.

The animals were divided over four groups of five animals each (see Table 1). The first group received the killed whole virus vaccine formulated in the commercially available adjuvant XSolve™ (available from MSD Animal Health, Boxmeer, The Netherlands), such that the final vaccine comprises 21% v/v of the non-metablizable oil Marcol™ 52 and 1.25% v/v of the metabolizable oil vitamin E acetate. The second group received the same antigen, formulated in the commercially available adjuvant Diluvac Forte™ (available from MSD Animal Health, Boxmeer, The Netherlands), such that the final vaccine comprises 7.5% v/v of the metabolizable oil vitamin E acetate. The third group received the same antigen formulated in the alum hydrogel containing vaccine ProSystem™ CE (available from Merck Animal Health, USA). The fourth group received the same antigen formulated in water without adjuvant.

TABLE 1

Overview of animal groups and their treatment

| Group | # piglets | PEDV antigen | Dose | Adjuvant |
|---|---|---|---|---|
| 1 | 5 | Killed whole virus | 1.5E7 TCID$_{50}$ | XSolve |
| 2 | 5 | Killed whole virus | 1.5E7 TCID$_{50}$ | Diluvac Forte |
| 3 | 5 | Killed whole virus | 1.5E7 TCID$_{50}$ | ProSystem CE |
| 4 | 5 | Killed whole virus | 1.5E7 TCID$_{50}$ | — |

Results
Body Temperature

An overview of the mean body temperatures per group are shown in Table 2. It can be concluded that none of the vaccines caused a serious temperature elevation of more the 1° C., and that XSolve induced the largest temperature increase of the three adjuvants tested. The highest individual temperature increase observed in this group was 1.7° C.

TABLE 2

Mean rectal temperatures taken after the first or second vaccination.

| | | Temperature after 1$^{st}$ vaccination | | | Temperature after 2$^{nd}$ vaccination | | |
|---|---|---|---|---|---|---|---|
| Group | Vaccine | t = 0 h | t = 4 h | t = 24 h | t = 0 h | t = 4 h | t = 24 h |
| 1 | XSolve | 39.60 | 40.02 | 39.94 | 39.94 | 40.72 | 40.20 |
| 2 | Diluvac Forte | 39.90 | 40.14 | 39.68 | 40.03 | 40.60 | 39.94 |
| 3 | ProSystem CE | 39.54 | 40.16 | 39.76 | 39.89 | 40.18 | 39.84 |
| 4 | No adjuvant | 39.90 | 39.84 | 39.52 | 39.76 | 40.31 | 39.88 |

Virus Neutralization Assay

Figure 1:
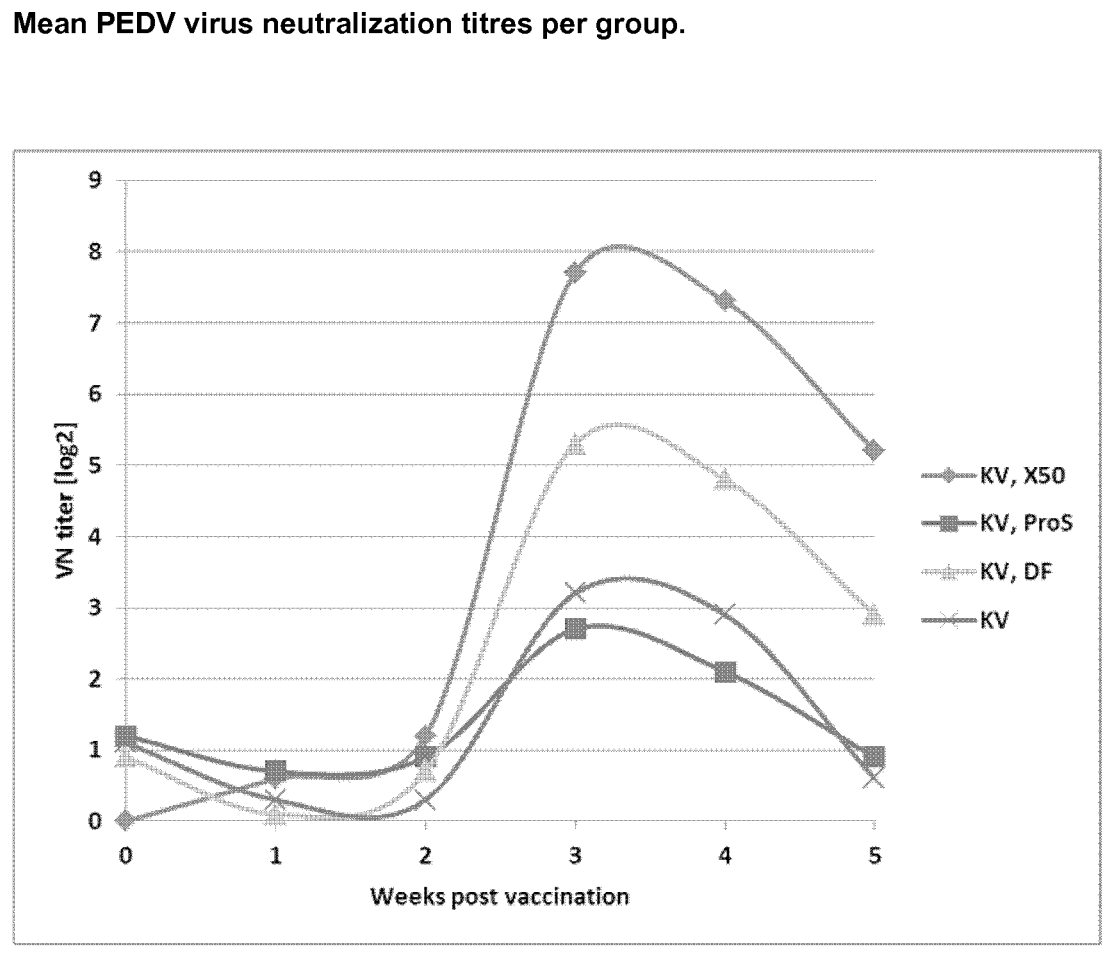

The calculated mean VN titres of each group are graphically presented in FIG. 1. It can be concluded that killed whole virus antigen is able to induce good VN titres. The contribution by the adjuvants is such that the adjuvant based on the non metabolizable oil gives the highest titres, followed by the adjuvant based on the metabolizable oil, thereafter followed by the adjuvant based on alum hydroxide gel.

Example 3 the Influence of the Type of Non-Live Antigen

Study Design

Sixty piglets seronegative for PEDV were available for this trial. When the piglets were approximately five weeks old they were immunized with 2 ml vaccine via the intramuscular (IM) route, and boosted three weeks thereafter. All applications were given into the neck. An overview of the experimental groups is given in Table 3. Blood samples were collected before the first vaccination, and two, three, four, five, and six weeks thereafter. Serum was collected from the blood samples and the virus neutralizing antibody titre was determined. Rectal temperatures were measured on the day of vaccination and 4 and 24 hours thereafter. After each vaccination all piglets were palpated at two, four, six, eight, ten, 12, and 14 days post vaccination on the site of administration.

TABLE 3

Overview of animal groups and their treatment

| | | Non live PEDV antigen | | |
|---|---|---|---|---|
| Group | # piglets | Name | Type | Dose (in 2 ml) |
| 1a | 5 | US S1 | full-length S1 of US strain | 10 µg |
| 1b | 5 | US S1-C | C-domain of S1 of US strain | 10 µg |
| 2a | 5 | US S1-pFc | full-length S1 of US strain + Fc domain of porcine IgG | 10 µg |
| 2b | 5 | US S1-Fc | full-length S1 of US strain + Fc domain of human IgG | 10 µg |
| 3a | 5 | US S1-C-Fc | C-domain of Spike of US strain + Fc domain of human IgG | 10 µg |
| 3b | 5 | US S1-N-Fc | N-domain of Spike of US strain + Fc domain of human IgG | 10 µg |
| 4 | 10 | DR13 KV | 1 mM BEI inactivated caDR13-ESMN-ΔORF3 | $6.0 \cdot 10^5$ TCID$_{50}$ |
| 5 | 10 | DR13 KV | 1 mM BEI inactivated caDR13-ESMN-ΔORF3 | $3.0 \cdot 10^6$ TCID$_{50}$ |
| 6 | 10 | DR13 KV | 1 mM BEI inactivated caDR13-ESMN-ΔORF3 | $1.5 \cdot 10^7$ TCID$_{50}$ |

Materials and Methods
Subunit Vaccines

The antigens present in the subunit vaccines used in this study were based on the S1 domain of the PEDV spike (5) protein. The S1 amino acid sequence was derived from a US isolate which is identical to the index strain USA/Colorado/2013. The full-length S1 domain as well as the N-terminal one-third or C-terminal two-third of the S1 domain were used. To facilitate protein purification and to improve immunogenicity, some S1 proteins were C-terminally tagged with an Fc fragment derived from either human or porcine immunoglobulins. All proteins were expressed in HEK293T cells, purified, and the protein content was determined. Briefly, the HEK293T cells were transfected with expression plasmids encoding the required polypeptide of PEDV (optionally with a mouse Fc tag). One day after transfection, cell culture fluid was replaced by fresh medium. Six days after transfection, the cell culture medium was collected and cleared by centrifugation. The polypeptide was subsequently purified by binding to protein-A sepharose beads. After allowing the polypeptide to bind to the beads, it was washed three times using PBS, and the polypeptide was eluted in 0.5M HAc pH 3. The pH was neutralized by using 3M Tris pH 8.8 (final pH 7.5). Finally, the polypeptide concentration was determined at $OD_{280}$ using a nanodrop. The polypeptide was stored at −80° C.

An overview of the S1 proteins is given in FIGS. 2A-2B. The subunit vaccines were formulated at 10 µg of S1 protein per 2 ml dose in XSolve.

Killed Virus Vaccines

The KV vaccines contained killed whole PEDV, inactivated with 1 mM BEI. The strain, cell culture adapted D13, shares 93.3% of its amino acids with USA/Colorado/2013. The KV antigens were formulated as a ready-to-use formulations in XSolve.

Virus Neutralization Assay

Sera were tested for the presence of neutralizing antibodies against PEDV using a virus neutralization (VN) assay on Vero cells. Briefly, serial two-fold dilutions of the test samples or reference sera were prepared in aMEM-TPB cell culture medium containing the antibiotics penicillin and streptomycin. Each dilution was mixed with an equal volume of 100 $TCID_{50}$ of an infectious PEDV strain that expresses green fluorescent protein (GFP) upon infection of susceptible Vero cells. After a pre-incubation period of 1 hour at 37° C., virus/serum dilution mixtures were transferred to 96-well microtitre plates containing Vero-CCL81 cells. After incubation for 48 hours at 37° C., the extent of GFP fluorescence indicative for virus replication was determined by microscopy. The antibody titre was calculated as log 2 (per 50 µl) of the reciprocal of the highest serum dilution where no virus replication could be demonstrated. Obtained VN titres are presented as averages calculated from duplicate measurements.

Pooled sera were tested in an alternative VN test that allows the use of either strain DR13 or strain GD01. Since GD01 requires trypsin for infection, the method described above was modified as follows: After co-incubation of 1 hour at 37° C., the virus/serum mixtures were left on the Vero-CCL81 cells for 2 hours at 37° C. Then the mixtures were removed, the cells were washed twice with PBS, and the cells were incubated at 37° C. for 48 hours in the presence of aMEM-TPB plus 10 µg/ml trypsin for GD01 (or aMEM-TPB without trypsin in case strain DR13 was used in this procedure).

PEDV Antibody ELISA

Antibodies in sera against the S1 part of the PEDV spike protein derived from strain USA/Colorado/2013 were determined in an antibody ELISA. For this, plates were coated with 100 µl of PEDV S1 (0.25 µg/ml). Sera were diluted 1:900 in PBS0/1% BSA and added to the coated wells followed by incubation for 1 hour at 37° C. After two washes with PBS0/0.05% Tween-20, 100 µl of rabbit αSwine IgG HRPO conjugate diluted 1:10,000 in PBS0/1% BSA/0.5% tween20 was added to the wells, and plates were incubated for 1 hour at 37° C. After three washes with PBS0/0.05% Tween-20, 100 µl/well of TMB "super slow" substrate was added to each well followed by incubation at room temperature for 10 min (in the dark). Reactions were stopped by adding 100 µl of 25% sulfuric acid per well. The optical density (OD) at 450 nm was measured with an ELISA reader. Sera from naturally infected pigs were included as positive controls.

Results

Body Temperature

An overview of the mean body temperatures per group are shown in Table 4. It can be concluded that none of the vaccines caused a serious mean temperature elevation of more the 1 degrees Celsius. The largest temperature increase was seen at 4 hours post-vaccination, but in most cases the temperature returned to normal levels at 24 hours post-vaccination. The highest individual temperature increase (2.3° C.) was observed for one animal in Group 6, 4 h after the booster vaccination.

Local Reactions

Animals were palpated on the site of intramuscular vaccine application at 2, 4, 6, 8, 10, 12, and 14 days post-vaccination. From the length and width (in cm), the surface of the local reaction (i.e. swelling) was calculated. One animal in Group 2b displayed a very mild (<1 $cm^2$) and transient (disappeared within a day) swelling directly after the booster vaccination. No local reactions were observed for all other 59 animals.

TABLE 4

Mean rectal temperatures taken after the first or second vaccination.

| Group | Vaccine | Temperature after 1st vaccination [° C.] | | | Temperature after 2nd vaccination [° C.] | | |
|---|---|---|---|---|---|---|---|
| | | t = 0 h | t = 4 h | t = 24 h | t = 0 h | t = 4 h | t = 24 h |
| 1a | US S1 | 39.60 | 39.68 | 39.84 | 39.74 | 40.52 | 39.64 |
| 1b | US S1-C | 39.34 | 39.92 | 39.52 | 39.50 | 40.02 | 39.78 |
| 2a | US S1-pFc | 39.60 | 40.18 | 39.90 | 39.98 | 40.18 | 39.70 |
| 2b | US S1-Fc | 39.86 | 40.08 | 39.90 | 39.82 | 40.26 | 39.48 |
| 3a | US S1-C-Fc | 39.60 | 39.96 | 40.14 | 39.46 | 40.22 | 39.44 |
| 3b | US S1-C-Fc | 39.58 | 39.62 | 39.80 | 39.72 | 40.10 | 39.56 |
| 4 | DR13 KV 6.0E5 | 39.28 | 40.04 | 39.55 | 39.84 | 40.49 | 39.57 |
| 5 | DR13 KV 3.0E6 | 39.51 | 39.92 | 39.62 | 39.60 | 40.05 | 39.46 |
| 6 | DR13 KV 1.5E7 | 39.25 | 39.94 | 39.77 | 39.84 | 39.81 | 39.61 |

Virus Neutralizing Antibodies

For the killed whole virus vaccines a virus neutralization assay was performed using the DR13 strain to be neutralized by the serum antibodies. The calculated mean VN titres of each group are presented in Table 5. From this table it can be concluded that DR13 KV antigen induced good VN titres in a clear dose responsive manner. It appears that a minimum dose corresponding to 3.0E6 $TCID_{50}$ killed whole PEDV is necessary to induce VN titres above 5 log 2. The result of this example confirms the results of Example 2.

TABLE 5

PEDV neutralizing antibody titres ($\log_2$/50 µl).

| Group | Vaccine | t = 4 | t = 5 | t = 6 |
|---|---|---|---|---|
| 4 | DR13 KV 6.0E5 | 2.8 | 3.9 | 3.3 |
| 5 | DR13 KV 3.0E6 | 5.5 | 6.0 | 5.5 |
| 6 | DR13 KV 1.5E7 | 8.6 | 8.8 | 8.1 |

Time (t) is indicated in weeks after the first vaccination.

For the subunit vaccines the alternative VN test was used. This is because the spike protein of the DR13-GFP strain used in the other VN test is about 93.3% identical to that of the US isolates from which the S1 subunits were derived and approximately 92.7% identical to spike of strain GD01. This sequence difference might explain why VN antibodies cannot be detected in the other test. Therefore, sera were pooled per group and the presence of serum neutralizing antibodies was determined in the alternative VN test that allows the use of either the DR13-GFP or GD01 strain. The results are summarized in Table 6.

TABLE 6

PEDV neutralizing antibody titres ($\log_2$/50 µl) in pooled sera.

| | | PEDV strain DR13-GFP | | | PEDV strain GD01 | | |
|---|---|---|---|---|---|---|---|
| Group | Vaccine | t = 4 | t = 5 | t = 6 | t = 4 | t = 5 | t = 6 |
| 1a | US S1 | 0.0 | 0.0 | 0.0 | 6.0 | 5.5 | 4.5 |
| 1b | US S1-C | 0.0 | 0.0 | 0.0 | 5.0 | 5.5 | 4.0 |
| 2a | US S1-pFc | 0.0 | 0.0 | 2.0 | 7.0 | 8.0 | 8.0 |
| 2b | US S1-Fc | 1.0 | 0.0 | 0.0 | 6.0 | 8.0 | 8.0 |
| 3a | US S1-C-Fc | 1.0 | 0.0 | 0.0 | 8.0 | 6.0 | 7.5 |
| 3b | US S1-N-Fc | 0.0 | 0.0 | 0.0 | 1.0 | 0.0 | 1.0 |

Time (t) is indicated in weeks after the first vaccination.

Indeed, the DR13 strain appears to be not suitable for detecting VN titres induced by the subunit vaccines. However, the DR13 neutralizing antibody titre in the pooled sera of the killed whole virus vaccines appeared to correspond well with the group averages of individually determined VN titres at 4, 5, and 6 weeks after the first vaccination (results no shown). This result demonstrates that (i) sera can be pooled to establish the VN titres per group, and (ii) the alternative VN assay for determining VN titres in pooled sera delivers similar results as the VN assay specifically developed for DR13-GFP. If the GD01 neutralizing antibody titre is determined, the picture for the S1 subunits (as shown in table 6, right hand side column) is as follows: With the exception of S1-N-Fc, they all induced a VN titre. The data show that (i) intact S1 or its C-terminal part are good antigens for triggering a VN antibody response, and (ii) a C-terminal extension with a Fc fragment improves the immune response.

Also, it is shown that 10 µg of the S1 subunits is able to induce a VN titer that at least the same as the level that can be obtained with a vaccine comprising per dose 3E06 $TCID_{50}$ killed whole PED virus. Thus, 10 µg of the S1 subunit is a dose that corresponds to at least 3E06 $TCID_{50}$ killed whole PED virus. To check this latter correspondence, a dose-response curve was made using the X-solve adjuvant and a dose range of 0.4 µg-2.0 µg-10 µg-50 µg of the S1 subunit. After IM vaccination (prime-boost scheme with interval of three weeks) the lower dosages led to maximum VN titres ($\log_2$/50 µl, 6 weeks post vaccination) of approximately only 1, whereas the 10 µg group had a VN titer of 6.5 and the 50 µg group had a VN titer of 7.0. This confirms that 10 µg of the S1 subunit is a dose that corresponds to at least 3E06 $TCID_{50}$ killed whole PED virus (i.e. the established minimum dose able to induce a VN titre of at least 5).

Antibodies Against the S1 Subunit of Spike

An ELISA was performed on the pooled sera mentioned above for the last two time-points after vaccination. The ELISA data corresponded well with the VN titres (see Table 7).

TABLE 7

$OD_{450}$ values of 1:900 diluted sera measured in the S1 ELISA.

| Group | Vaccine | t = 5 | t = 6 |
|---|---|---|---|
| 1a | US S1 | 3.026 | 3.366 |
| 1b | US S1-C | 2.88 | 3.075 |
| 2a | US S1-pFc | 3.087 | 3.298 |
| 2b | US S1-Fc | 2.848 | 2.697 |
| 3a | US S1-C-Fc | 2.952 | 2.994 |
| 3b | US S1-N-Fc | 0.305 | 0.326 |

Time (t) is indicated in weeks after the first vaccination.

The invention claimed is:

1. A method to protect a pig against an infection with porcine epidemic diarrhea virus (PEDV) comprising administering to the pig a vaccine comprising non-live PEDV antigen and a non-metabolizable oil containing adjuvant, wherein the total amount of oil in the vaccine is less than 50% v/v, and the antigen is administered at a dose corresponding to at least 3.0E6 $TCID_{50}$ killed whole PEDV.

2. The method of claim 1, wherein the dose of the antigen corresponds to at least 1.5E7 $TCID_{50}$ killed whole PEDV.

3. The method of claim 1, wherein the total amount of the oil is less than 40% v/v.

4. The method of claim 1, wherein the oil is emulsified in an hydrophilic solvent.

5. The method of claim 1, wherein the vaccine in addition to the non-metabolizable oil comprises vitamin E acetate.

6. The method of claim 1, wherein the antigen contains a polypeptide that corresponds to the C terminal two-third of the S1 domain of the spike protein of PEDV.

7. The method of claim 6, wherein the polypeptide corresponds to the S1 domain of the spike protein of PEDV.

8. The method of claim 7, wherein the polypeptide corresponds to the spike protein of PEDV.

9. The method of claim 1, wherein the antigen is killed whole PEDV.

10. A vaccine to protect a pig against an infection with porcine epidemic diarrhea virus (PEDV) comprising non-live PEDV antigen and a non-metabolizable oil containing adjuvant, wherein the total amount of oil in the vaccine is less than 50% v/v, and the antigen is present in a concentration corresponding to at least 1.5E6 $TCID_{50}$ killed whole PEDV per ml.

* * * * *